United States Patent [19]

Fei

[11] Patent Number: 4,547,075
[45] Date of Patent: Oct. 15, 1985

[54] DEVICE FOR THE DETECTION AND CALCULATION OF PARTICLES PRESENT IN A MOVING SUSPENSION FOR HEMATOLOGICAL ANALYSES AND THE LIKE

[75] Inventor: Alberto Fei, Florence, Italy

[73] Assignee: Dr. Alberto Ciampolini Strumenti Scientifici, Italy

[21] Appl. No.: 580,890

[22] Filed: Feb. 16, 1984

[30] Foreign Application Priority Data

Feb. 23, 1983 [IT] Italy .................... 9347 A/83

[51] Int. Cl.⁴ .................................... G01N 21/00
[52] U.S. Cl. ...................... 356/440; 356/39; 356/72; 356/73; 356/246; 356/442
[58] Field of Search ............ 356/440, 442, 72, 73, 356/39, 246

[56] References Cited

U.S. PATENT DOCUMENTS 3,800,147  3/1974  Shea et al. .................. 356/442 X
4,367,043  1/1983  Sweet et al. ................. 356/440 X Primary Examiner—Bernard D. Pianalto
Attorney, Agent, or Firm—McGlew and Tuttle

[57] ABSTRACT

A blade or thin beam of concentrated coherent light is formed in order to detect and calculate the number of particles present in a moving suspension that flows through a suspension conduit featuring a relatively small section and which is made of optically transparent material. This beam extends through the entire section at a reduced thickness and in the flow direction. A suitable detector detects and counts the particles that move across the blade, operated by the absorption of light that occurs when each individual particle passes through it.

4 Claims, 2 Drawing Figures

DEVICE FOR THE DETECTION AND CALCULATION OF PARTICLES PRESENT IN A MOVING SUSPENSION FOR HEMATOLOGICAL ANALYSES AND THE LIKE

BACKGROUND OF THE INVENTION

The invention concerns both the system and device which, with the aid of a blade of coherent light (laser or suchlike), are used to detect and count the particles present in a moving liquid or gaseous suspension.

SUMMARY OF THE INVENTION

The system according to the invention calls for the formation of a blade or very thin beam of coherent light in connection with a suspension flow conduit or counting channel with a relatively small section made of optically transparent material. This blade extends over the entire conduit section at a reduced thickness in the flow direction. The absorption of light provoked by the passage of each individual particle through the blade of light activates the detection and counting of the particles.

The device according to the invention used to implement the system described above includes a combination of the following basic means; a body transparent reading cell containing a counting channel or conduit with a limited section in which the suspension to be examined flows; optical means which are able to form a blade of coherent light with a reduced thickness, placed transversally with regard to the abovementioned conduit; and sensor means (especially photoelectric means) used to detect any attenuation of light due to the passage of the particles.

In practice, the abovementioned optic devices used to produce coherent light may include a diaphragm with a louver extending out in the direction of the counting channel and an optic system that compresses the coherent light beam towards the largest opening size in order to form the reduced-thickness blade of condensed light.

The above conduit or counting channel has advantageously a rectangular section with sides parallel to the optic system axis.

BRIEF DESCRIPTION OF THE DRAWINGS

The invention is easier to understand by following the description provided herein and the attached drawing, which shows a practical non-restrictive embodiment of the invention.

DESCRIPTION OF THE PREFERRED EMBODIMENT

Figure 1:
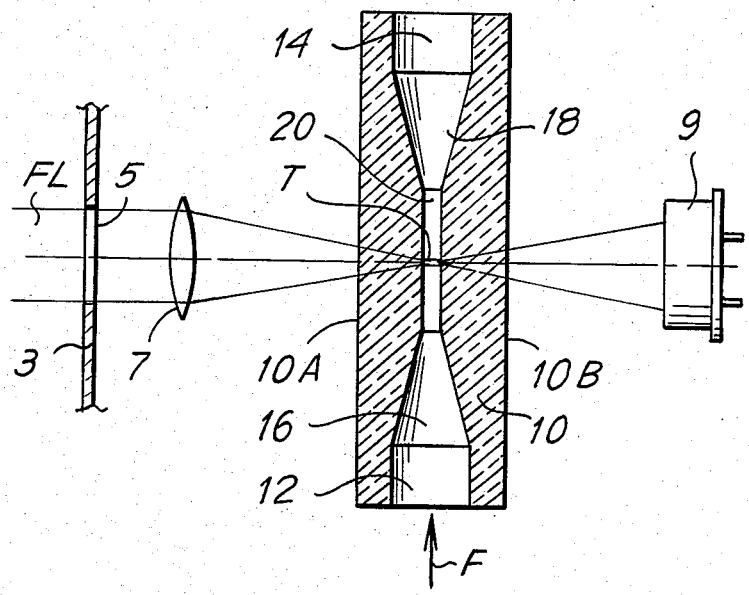
FIGS. 1 and 2 show an explanatory diagram of the main components of the device, presented in both a lateral and axial view with respect to the flow direction of the suspension to be analyzed.
Figure 2:
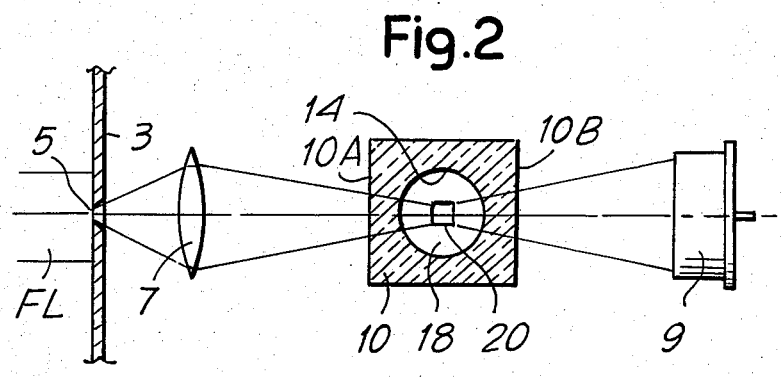

In the illustrated diagram, FL indicates a beam of coherent light (a He-Ne laser, a semiconductor laser, or suchlike), which is shuttered by screen 3, complete with a slit 5, which, in turn, extends parallel to the flow direction of the liquid or gaseous particles suspension, this direction being indicated by arrow F. Numeral 7 indicates a generic laser optical system, while 9 indicates a photosensitive detector which reacts to the same wave length as the coherent light.

The suspension to be analyzed flows through a conduit (i.e. a counting channel) made from a block of material 10 which is either transparent or sufficiently permeable to allow the passage of the band FL energy. In particular, block 10 features two flat external walls, 10A and 10B, which are set at right angles to the FL-band optical system axis. However, it is not excluded that surfaces 10A and 10B may be part of the optical system. A conduit is scooped out in block 10; the relatively wide entrance and exit sections of the conduit are indicated by 12 and 14 and funnel-shaped coupling zones are indicated by 16 and 18. Numeral 20, indicates a reduced-section zone, rectangular shaped in the section at right angles to the suspension flow, which constitutes the counting channel.

The optic system, which is pierced by the coherent light (laser) FL is extended in order to concentrate the blade of light formed by slit 5 in such a way that an extremely reduced coherent light thickness is created perpendicular to the flow direction in conduit 20, and that the thickness covers the entire section of said conduit.

In substance, the flow of extremely condensed light sets up a very thin sight T in conduit 20; this sight covers the entire section and is pierced in a perpendicular sense by the particles. A particle which pierces the thickness of the blade of light (i.e. the lighted sight T) provokes an attenuation of the light flow, which is then picked up by detector 9 and, hence, may be revealed, memorized and calculated by means of the signal obtained through the abovementioned attenuation process. The attenuation that may be valued is in the range of a mere one one-hundredth or few one-hundredths of the energy received in the absence of a particle in the sight T.

The section of the conduit zone, or counting channel 20, has proved sufficiently large to avoid any difficulties in suspension movements in the direction F of the particle flow. In fact, this has been one of the most frequently mentioned drawbacks of other existing hematological equipment.

The functioning of the device is based on the absorption of light provoked by the passage of particles through a thin blade T of coherent light (a He-Ne laser or semiconductor laser), which is picked up by photoelectric sensor 9. The device's sensitivity to particle size (measured in the microns-of-diameter range) is a function of the height and width of the blade of light T; in practice, it is a ratio between the surface (or volume) of the particle and the surface of the projected ray of light. Roughly 1/100 is considered a suitable ratio for good detection.

Advantageously the size of sight T (the blade of light), measured in terms of the thickness of the coherent beam in the particle passage direction, will be kept as small as possible in order to cut down the probability of simultaneous passage of more than one particle and, therefore, overlapping absorption values.

By specially calibrating detection system 9 (which proves necessary when certain kinds of particles are measured: for example, if different absorption values are provoked by similarly-sized particles), it is even possible to define the volume of moving particles, since the amount of light absorbed is proportional to the volume and the particles may be considered virtually spherical in shape.

Counting conduit 20 sizes (with an orthogonal section with respect to the liquid flow) must be as small as possible without, however, hindering the passage of either liquids or gas; furthermore, conduit 20 features an advantageously rectangular shape.

By measuring the volume of the sample that passes through the channel and is read, it is easy to obtain the particle number in volume.

Structure 10 of the counting channel is carried out with an entrance funnel and a reduced section in zone 20, no matter what the device's application. These features insure strong flow acceleration in the actual counting channel 20. In addition, channel 20 must feature perfect optical characteristics and perfect transparency. The reduced transversal dimensions of channel 20 also produce an adequately restricted depth of field.

One practical application of this system is in detecting hematological data; however, other applications for many fields of analysis are also possible.

It should be understood that the drawing shows but one example of a practical demonstration of the device, which can in fact vary in form and layout, without coming out from the scope of the idea that inform the invention.

I claim:

1. A device for detecting particles suspended in a flow medium comprising:
    a block defining a flow conduit therein for the passage of the flow medium with suspended particles, in a flow direction through the block, said flow conduit comprising an entrance section for receiving the flow medium, a first funnel-shaped coupling zone connected to said entrance section, a counting channel connected to said first funnel-shaped coupling zone, a second funnel-shaped coupling zone connected to said counting channel and an exit section connected to said second funnel-shaped coupling zone, said counting channel having a cross-section transverse to the flow direction which is rectangular and which is small with respect to a cross-section of said entrance and exit sections, said block being transparent to coherent light in the direction transverse to said flow direction and at least through said counting channel;
    a source of coherent light on one side of said block for generating a beam of coherent light;
    optic means positioned between said source of coherent light and said block for focusing said beam of coherent light into a thin flat blade of light which passes transversely to said flow direction through said counting channel, said blade of light having a thickness in said flow direction which is small with respect to a width of said counting channel transversely to the flow direction, said optic means forming said blade of light to span the entire cross-section of said counting channel transverse to said flow direction; and
    a photodetector on the side of said block opposite from said optic means for receiving said blade of light from said counting channel, said photodetector being capable of detecting a fluctuation in light from said beam of light caused by the passage of a single particle suspended in the flow medium, and counting said fluctuations for providing a numeric count of particles suspended in the flow medium as the flow medium passes in the flow direction through said counting channel.

2. A device according to claim 1, wherein the thickness of said blade of light and particles suspended in said flow medium are on the order of microns, a ratio of the thickness of said blade of light in the flow direction to the width of said blade of light transversely to the flow direction in said counting chamber being about 1 to 100.

3. A device according to claim 2, wherein said optic means includes a diaphragm with a louver lying in the flow direction outside said block for forming the blade of light.

4. A device according to claim 3, wherein said block has outside walls adjacent said counting channel and between said optic means and said photodetector which are planar and lie parallel to the flow direction, two walls of said rectangular cross-sectioned counting channel lying parallel to said block of light and two walls of said counter channel lying perpendicularly to said blade of light.

* * * * *